United States Patent [19]

Robertson

[11] Patent Number: 4,647,564

[45] Date of Patent: Mar. 3, 1987

[54] INOTROPIC AGENTS

[75] Inventor: David W. Robertson, Indianapolis, Ind.

[73] Assignee: Eli Lilly and Company, Indianapolis, Ind.

[21] Appl. No.: 836,656

[22] Filed: Mar. 5, 1986

Related U.S. Application Data

[63] Continuation of Ser. No. 718,577, Apr. 1, 1985, abandoned, which is a continuation-in-part of Ser. No. 610,210, May 14, 1984, abandoned.

[51] Int. Cl.$^4$ ................... A61K 31/50; C07D 401/10
[52] U.S. Cl. .................. 514/254; 514/227; 514/239; 544/114; 544/238; 544/239
[58] Field of Search .............. 514/254, 227, 239; 544/114, 238, 239

[56] References Cited

U.S. PATENT DOCUMENTS

| | | | |
|---|---|---|---|
| 3,845,050 | 10/1974 | Lebkuecher et al. | 260/250 A |
| 4,258,185 | 3/1981 | Nakao et al. | 544/114 |
| 4,304,777 | 12/1981 | Lesher et al. | 424/250 |
| 4,353,905 | 10/1982 | Sircar et al. | 424/250 |
| 4,361,563 | 11/1982 | Austel et al. | 424/250 |
| 4,397,854 | 8/1983 | Sircar | 424/250 |
| 4,404,203 | 9/1983 | Sircar | 424/250 |
| 4,474,785 | 10/1984 | Rossy et al. | 424/250 |
| 4,562,190 | 12/1985 | Ueda et al. | 514/254 |
| 4,591,591 | 5/1986 | Robertson | 514/254 |

FOREIGN PATENT DOCUMENTS

| | | |
|---|---|---|
| 68310 | 1/1983 | European Pat. Off. |
| 588016 | 7/1981 | Japan |

OTHER PUBLICATIONS

Curran et al., *J. Med. Chem.*, 17(3), 273 (1974).
McEvoy et al., *J. Med. Chem.*, 17(3), 281 (1974).
Derwent 27593K/12 abstracting German OLS No. 3,135,617.
Derwent 18918K/08 abstracting Japanese Pat. No. J58008016.

*Primary Examiner*—Veronica P. Hoke
*Attorney, Agent, or Firm*—Robert A. Conrad

[57] ABSTRACT

This invention provides certain pyridazinone derivatives, their pharmaceutical formulations, and their use as positive inotropic agents.

20 Claims, No Drawings

INOTROPIC AGENTS

This application is a continuation of application Ser. No. 718,577, filed Apr. 1, 1985, which is a continuation-in-part of application Ser. No. 610,210, filed May 14, 1984, all now abandoned.

BACKGROUND OF THE INVENTION

The cardiac glycosides and the sympathomimetic amines are the principal inotropic agents used in the management of congestive heart failure. Although the cardiac glycosides, especially digitalis, are among the most frequently prescribed drugs, they have numerous liabilities such as a low therapeutic index and erratic absorption, and are associated with life-threatening arrhythmias and deleterious drug-drug interactions. In addition, many patients either do not respond, or become refractory to these agents. The sympathomimetic amines, such as dopamine and epinephrine, have limited utility due to positive chronotropic effects, arrhythmogenic properties, and oral ineffectiveness.

More recently, new classes of inotropic agents have been found. These include certain dihydropyridazinone derivatives such as these taught in U.S. Pat. Nos. 4,353,905, 4,361,563, 4,304,777, and 4,404,203 which cause an increase in myocardial contractility in anesthetized dogs and cats. Other pyridazinone derivatives are taught in the art to be cardiotonics, antihypertensives, and antithrombotic agents; see, e.g., U.S. Pat. No. 4,258,185.

The present invention provides certain pyridazinone derivatives which are potent, long-acting, orally effective positive inotropic agents which cause minimal effects on blood pressure and heart rate.

SUMMARY OF THE INVENTION

This invention provides compounds of Formula I

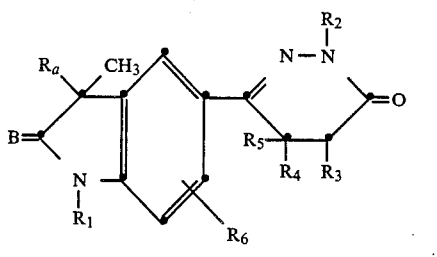

wherein
$R_a$ is hydrogen or methyl;
$B=C<$ is $O=C<$ or $H_2C<$;
$R_1$ is hydrogen, $C_1$-$C_4$ alkyl, $C_2$-$C_4$ alkanoyl, methyl- or ethyl-sulfonyl, or benzoyl optionally substituted on the phenyl ring with one to three substitutents selected from halo, $C_1$-$C_4$ alkyl, methoxy or ethoxy;
$R_2$ is hydrogen, $C_1$-$C_{22}$ alkyl, hydroxy-substituted $C_1$-$C_3$ alkyl, carbamoyl-substituted $C_1$-$C_{11}$ alkyl, naphthyloxy-methyl or -ethyl, an oxo-substituted $C_1$-$C_{11}$ alkyl group, or $R_6R_7N$-$(CH_2)_n$— where each of $R_6$ and $R_7$ is independently hydrogen or $C_1$-$C_4$ alkyl, or when taken together with the nitrogen atom to which they are attached form pyrrolidino, piperidino, morpholino, piperazino, or N-methylpiperazino ring, and n is 2 or 3;
$R_3$ is hydrogen or methyl;
$R_4$ is hydrogen, $C_1$-$C_4$ alkyl, hydroxymethyl, or $C_2$-$C_4$ alkanoyloxymethyl;
$R_5$ is hydrogen or $C_1$-$C_4$ alkyl;
or $R_3$ and one of $R_4$ and $R_5$ taken together form a bond;
$R_6$ is hydrogen or methyl; and pharmaceutically acceptable salts thereof.

This invention also provides a method of producing a positive inotropic effect on a mammal, including a human subject, which comprises administering to said mammal an effective amount of a compound of this invention.

According to a further aspect of the present invention, there are provided pharmaceutical formulations which comprise as active ingredient a compound of Formula I in association with a pharmaceutically acceptable carrier, diluent, or excipient therefor.

DETAILED DESCRIPTION AND PREFERRED EMBODIMENTS

A preferred group of compounds are those of the above formula wherein
(a) $R_a$ is methyl;
(b) $B=C<$ is $O=C<$;
(c) each of $R_1$, $R_2$, $R_3$, and one of $R_4$ and $R_5$ is hydrogen;
(d) the other of $R_4$ and $R_5$ is hydrogen or methyl; and
(e) $R_6$ is hydrogen. Especially preferred are 1,3-dihydro-3,3-dimethyl-5-(1,4,5,6-tetrahydro-6-oxo-3-pyridazinyl)-2H-indol-2-one and 1,3-dihydro-3,3-dimethyl-5-(1,4,5,6-tetrahydro-4-methyl-6-oxo-3-pyridazinyl)-2H-indol-2-one, and the pharmaceutically acceptable salts thereof.

The following definitions refer to the various terms used throughout this disclosure.

The term "$C_1$-$C_{22}$ alkyl" refers to the straight and branched aliphatic radicals of one to twenty-two carbon atoms, and includes methyl, ethyl, propyl, isopropyl, butyl, isobutyl, sec-butyl, tert-butyl, pentyl, hexyl, heptyl, octyl, nonyl, decyl, pentadecyl, octadecyl, eicosyl, and docosyl. This term includes within it the terms "$C_1$-$C_3$ alkyl," "$C_1$-$C_4$ alkyl," and "$C_1$-$C_{11}$ alkyl."

The term "$C_2$-$C_4$ alkanoyl" refers to acetyl, propionyl, or butyryl. The term "$C_2$-$C_4$ alkanoyloxymethyl" refers to acetoxymethyl, propionyloxymethyl, or butyryloxymethyl. The term "halo" refers to fluoro, chloro, or bromo.

The compounds of the present invention can be prepared by any of several methods known to those skilled in the art. In addition to their utility as inotropic agents, some of the compounds of the present invention are also useful as intermediates to other compounds of the invention. Such intraconversions may be performed by the appropriate sequences of esterification, alkylation, acylation, sulfonation, dehydrogenation, or related reactions as are known to those skilled in the art. For example, compounds where $R_1$ or $R_2$ is hydrogen may be alkylated, acylated, sulfonylated, etc. to provide the corresponding compounds of this invention wherein $R_1$ or $R_2$ is alkyl, alkanoyl, benzoyl, sulfonyl, etc. as previously defined. Similarly, the carbonyl derivatives of Formula I ($B=C<=O=C<$) may be reduced to the methylene compounds ($B=C<=H_2C<$) by standard reductive techniques known in the art.

A preferred method of making the compounds of Formula I comprises reacting the appropriately N-substituted indoline or indol-2-one (II), with a maleic or succinic anhydride derivative (III), in the presence of a Lewis acid such as aluminum chloride, and in the presence of a nonreactive solvent, for example a halogenated alkane such as 1,1,2,2-tetrachloroethane, a dialkylformamide such as dimethylformamide, or the like, as summarized in Scheme I.

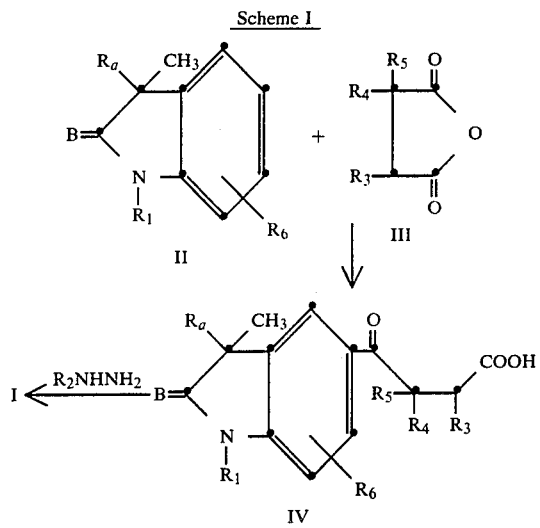

This reaction is a standard Friedel-Crafts acylation reaction and is generally complete within about 24 hours when carried out at a temperature from about 25° C. up to the reflux temperature of the reaction mixture, for example about 150°. This reaction provides the corresponding gamma-keto-acid IV, which can be reacted with a hydrazine derivative $R_2NHNH_2$ (or hydrazine hydrate when $R_2$ is H) in the absence of a solvent, or if preferred in the presence of an inert solvent such as water, an alcohol, tetrahydrofuran, toluene, dimethylformamide, or the like, at a temperature ranging from about 20° C. to the reflux temperature of the reaction mixture. The compounds thus formed are compounds of Formula I. When $R_2$ is hydrogen, the resulting compound may be further transformed to other compounds of Formula I by other methods as previously described.

Where intermediate III is unsymmetrical, two possible products from the acylation are possible. In such cases, acylation of II with intermediate V

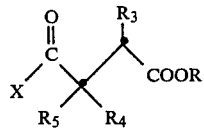

where X is bromo or chloro and R is, for example, $C_1$-$C_4$ alkyl, preferably methyl or ethyl, under standard acylation conditions, gives the ester derivative of intermediate IV which can be transformed into I ($R_2$=H) in the same way as previously described.

In addition, other methods of transforming II into I are generally taught in U.S. Pat. No. 4,258,185.

Intermediates II, III, and V and other required reagents are commercially available, are known in the literature, or can be prepared by methods known in the literature or by the methods described in the following examples. A preferred method of preparing 3-methyl- and 3,3-dimethyl-2-indolinone (II, B=C< =O=C< and $R_1$=H) comprises treating oxindole with one or two molar equivalents, respectively, of a strong base such as n-butyllithium and an inert solvent followed by the addition of one or two equivalents, respectively, of a methyl halide, such as methyl iodide. Surprisingly, the alkylation occurs solely on the carbon atom and no N-alkylation is seen.

Alternatively, 3-methyl- and 3,3-dimethyl-2-indolinone may be prepared by treating aniline with an α-bromo acid bromide (VI) under standard acylation conditions to provide amide VII which can then be ring closed to II (B=C< =O=C< and $R_1$=H) upon treatment with a Lewis acid, especially aluminum chloride, in a non-reactive solvent, preferably methylene chloride.

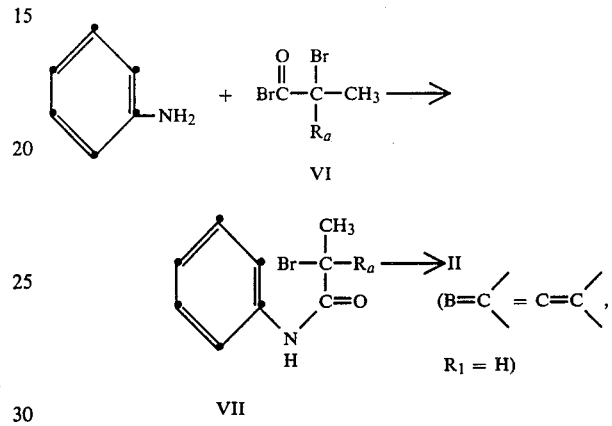

Depending upon the definitions of $R_a$, $R_3$, $R_4$, and $R_5$, the compounds of Formula I may exist as stereoisomers. This invention is not limited to any particular isomer but includes all possible individual isomers and racemates of the compounds of Formula I.

The pharmaceutically acceptable acid addition salts of this invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, and the like. Typical pharmaceutically acceptable salts of the invention thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycolate, malate, tartrate, methanesulfonate, propanesulfonate, naphthalene-1-sulfonate, naphthalene-2-sulfonate and the like salts. The preferred salts of this invention are those derived from inorganic acids, especially hydrochloric acid.

The following examples further illustrate the preparation of the compounds of this invention. The examples are illustrative only and are not intended to limit the scope of the invention in any way.

EXAMPLE 1

1,3-Dihydro-3,3-dimethyl-5-(1,4,5,6-tetrahydro-6-oxo-3-pyridazinyl)-2H-indol-2-one A. Preparation of 1,3-dihydro-3,3-dimethyl-5-(4-ketobutanoic acid)-2H-indol-2-one.

Dimethylformamide (3.6 ml) was added dropwise to 22.0 g of anhydrous aluminum chloride. An exotherm resulted, and the temperature of the slurry increased from room temperature to 40° C. To this slurry was added a mixture of succinic anhydride (1.65 g) and 3,3-dimethyl-2-indolinone (2.67 g). The mixture was stirred for one hour at 40° C. and then at 90° C. for 2.5 hours. The reaction mixture was slowly poured into 400 ml of ice, after which 50 ml of concentrated hydrochloric acid were added. The mixture was cooled overnight, and the resulting precipitate was recovered by filtration. The product was crystallized from dimethylformamide/water to provide 3.6 g of the desired subtitle intermediate as an off-white powder.

B. Preparation of 1,3-dihydro-3,3-dimethyl-5-(1,4,5,6-tetrahydro-6-oxo-3-pyridazinyl)-2H-indol-2-one.

To a slurry of 3.6 g of the intermediate from Example 1(A) above in 250 ml of absolute ethanol were added 1.8 ml of hydrazine hydrate. The reaction mixture was heated at reflux for 16 hours, cooled to room temperature, and the resulting precipitate was recovered by filtration. Crystallization from dimethylformamide/water provided 1.8 g of the desired title product as a white powder. m.p. >300° C.

Analysis for $C_{14}H_{15}N_3O_2$: Calc.: C, 65.36; H, 5.88; N, 16.33; Found: C, 65.14; H, 5.76; N, 16.05.

The following compounds can be prepared according to the synthesis as described in Example 1 or by other methods generally known in the art.

1,3-dihydro-3,3-dimethyl-5-(1,4,5,6tetrahydro-4-methyl-6-oxo-3-pyridazinyl)-2H-indol-2-one, 1,3-dihydro-3,3-dimethyl-5-(1,6-dihydro-6-oxo-3-pyridazinyl)-2H-indol-2-one, 3,3-dimethyl-5-(1,4,5,6-tetrahydro-6-oxo-3-pyridazinyl)indoline, 1,3-dihydro-1-acetyl-3,3-dimethyl-5-(1,4,5,6-tetrahydro-4,4-dimethyl-6-oxo-3-pyridazinyl)-2H-indol-2-one, 1-isopropyl-3,3-dimethyl-5-(1,4,5,6-tetrahydro-1-octyl-4-hydroxymethyl-6-oxo-3-pyridazinyl)indoline, 1-(4-chlorobenzoyl)-3,3-dimethyl-5-[1,6-dihydro-1-(3-piperidinopropyl)-6-oxo-3-pyridazinyl]indoline, 1-methylsulfonyl-3,3-dimethyl-5-[1,4,5,6-tetrahydro-1-(2-naphthyloxymethyl)-4-ethyl-4-methyl-6-oxo-3-pyridazinyl]indoline, 1,3-dihydro-1-(3-methoxy-4-methylbenzoyl)-3,3-dimethyl-5-(1,6-dihydro-4-butyl-6-oxo-3-pyridazinyl)-2H-indol-2-one, 1-isobutanoyl-3,3-dimethyl-5-(1,4,5,6-tetrahydro-4-methyl-4-propanoyloxymethyl-6-oxo-3-pyridazinyl)indoline, 1-isopropyl-3,3-dimethyl-5-[1,6-dihydro-1-(4-carbamoylhexyl)-4-ethyl-6-oxo-3-pyridazinyl]indoline, 1,3-dihydro-3,3-dimethyl-5-(1,4,5,6-tetrahydro-1,4,4-trimethyl-6-oxo-3-pyridazinyl)-2H-indol-2-one, 1-methylsulfonyl-3,3-dimethyl-5-[1,6-dihydro-1-(4-oxooctyl)-6-oxo-3-pyridazinyl]indoline, and 1,3-dihydro-1-ethyl-3,3-dimethyl-5-[1,4,5,6-tetrahydro-1-(3-hydroxypropyl)-4-butyl-6-oxo-3-pyridazinyl]-2H-indol-2-one.

EXAMPLE 2

1,3-Dihydro-1,3,3-trimethyl-5-(1,4,5,6-tetrahydro-6-oxo-3-pyridazinyl)-2H-indol-2-one A. Preparation of 1,3,3-trimethyloxindole.

A solution of 30.0 g of oxindole in 300 ml of dimethylformamide was added to a slurry of 31.5 g of sodium hydride in 200 ml of dimethylformamide cooled to 0° C. After hydrogen evolution ceased, 69.9 ml of methyl iodide were added to the reaction mixture. The mixture was stirred for three hours at room temperature, diluted with water, and extracted with ethyl acetate. The organic extract was washed with water and a saturated sodium chloride solution, dried over magnesium sulfate, and concentrated to dryness. The crude product was chromatographed over silica gel to provide 32.6 g of the desired subtitle intermediate as a red oil.

Analysis for $C_{11}H_{13}NO$: Calc.: C, 75.40; H, 7.48; N, 7.99; Found: C, 75.37; H, 7.42; N, 7.80.

B. Preparation of 1,3-dihydro-1,3,3-trimethyl-5-(4-ketobutanoic acid)-2H-indol-2-one.

Following the procedure of Example 1A, 10.0 g of 1,3,3-trimethyloxindole and 5.72 g of succinic anhydride were added to a melt of 12.5 ml of dimethylformamide and 76.2 g of anhydrous aluminum chloride. The reaction mixture was worked up in the same way as Example 1A to provide 11.8 g of the desired subtitle intermediate, m.p. 162°–163° C.

Analysis for $C_{15}H_{17}NO_4$: Calc.: C, 65.44; H, 6.22; N, 5.09; Found: C, 65.45; H, 6.29; N, 4.99.

C. Preparation of 1,3-dihydro-1,3,3-trimethyl-5-(1,4,5,6-tetrahydro-6-oxo-3-pyridazinyl)-2H-indol-2-one.

Following the procedure of Example 1B, 11.6 g of 1,3-dihydro-1,3,3-trimethyl-5-(4-ketobutanoic acid)-2H-indol-2-one and 5.5 ml of hydrazine hydrate were heated to reflux for four hours in 500 ml of ethanol.

Upon cooling, 7.0 g of the desired title product precipitated from solution which was recovered by filtration, m.p. 247°–248° C.

Analysis for $C_{15}H_{17}N_3O_2$: Calc.: C, 66.40; H, 6.32; N, 15.49; Found: C, 66.69; H, 6.06; N, 15.42.

EXAMPLES 3–8

The following compounds were prepared according to the procedures of Example 1 employing the appropriately substituted indolone and anhydride reagents. Yields are calculated for the final step, i.e., the reaction of the 4-ketobutanoic acid intermediate with hydrazine.

3. 1,3-Dihydro-1,3,3-trimethyl-5-(1,4,5,6-tetrahydro-4-methyl-6-oxo-3-pyridazinyl)-2H-indol-2-one, 64% yield, m.p. 225°–226° C.

Analysis for $C_{16}H_{19}N_3O_2$: Calc.: C, 67.35; H, 6.71; N, 14.73; Found: C, 67.45; H, 6.87; N, 14.61.

4. 1,3-Dihydro-3,3,7-trimethyl-5-(1,4,5,6-tetrahydro-6-oxo-3-pyridazinyl)-2H-indol-2-one, 93% yield, m.p. >300° C.

Analysis for $C_{15}H_{17}N_3O_2$: Calc.: C, 66.40; H, 6.32; N, 15.49; Found: C, 66.41; H, 6.32; N, 15.21.

5. 1,3-Dihydro-3,3,6-trimethyl-5-(1,4,5,6-tetrahydro-6-oxo-3-pyridazinyl)-2H-indol-2-one, 58% yield, m.p. 285° C. with decomposition.

Analysis for $C_{15}H_{17}N_3O_2$: Calc.: C, 66.40; H, 6.32; N, 15.49; Found: C, 66.43; H, 6.15; N, 15.68.

6. 1,3-Dihydro-3,3-dimethyl-5-(1,4,5,6-tetrahydro-5-methyl-6-oxo-3-pyridazinyl)-2H-indol-2-one, 59% yield, m.p. 273°–274° C.

Analysis for $C_{15}H_{17}N_3O_2$: Calc.: C, 66.40; H, 6.32; N, 15.49; Found: C, 66.11; H, 6.24; N, 15.25.

7. 1,3-Dihydro-3,3-dimethyl-5-(1,4,5,6-tetrahydro-4-methyl-6-oxo-3-pyridazinyl)-2H-indol-2-one, 85% yield, m.p. 273°–276.5° C. Analysis for $C_{15}H_{17}N_3O_2$: Calc.: C, 66.40; H, 6.32; N, 15.49; Found: C, 65.31; H, 6.30; N, 14.50.

8. 1,3-Dihydro-3-methyl-5-(1,4,5,6-tetrahydro-6-oxo-3-pyridazinyl)-2H-indol-2-one, 76% yield, m.p. >300° C.

Analysis for $C_{13}H_{13}N_3O_2$: Calc.: C, 64.19; H, 5.39; N, 17.27; Found: C, 63.91; H, 5.56; N, 17.12.

The compounds of Formula I are particularly useful as inotropic agents due to their potency, long action of effect, and oral efficacy and are therefore useful in the treatment and prevention of heart failure. For example, the compounds of this invention were examined as to their pharmacodynamic effects on the following test systems. For comparison, 1,3-dihydro-5-(1,4,5,6-tetrahydro-6-oxo-3-pyridazinyl)-2H-indol-2-one (Compound A) and 4,4-dimethyl-1,2,3,4-tetrahydro-6-(1,4,5,6-tetrahydro-6-oxo-3-pyridazinyl)quinolin-2-one (Compound B) as taught in U.S. Pat. No. 4,258,185 (although named somewhat differently), were also tested.

Positive Inotropic Activity in Isolated Cat Papillary Muscles

Cats of either sex were anesthetized with Metofane (1,1-difluoro-2,2-dichloroethyl methyl ether, Pittman-Moore). Their hearts were immediately removed and the papillary muscles dissected and suspended in individual organ baths. A platinum hook secured one end of the muscle to an electrode mounted in the bottom of the bath, and a silk thread attached the tendon to a Statham isometric transducer. The baths contained Krebs-Henseleit solution (36° C., bubbled with 95 percent oxygen—5 percent carbon dioxide) of the following millimolar composition: NaCl, 118; KCl, 4.5; $CaCl_2$, 2.5; $KH_2PO_4$, 1.1; $MgSO_4$, 1.2; $NaHCO_3$, 25; and glucose, 11.

A base-line tension of 1.5 g was applied to each muscle. Square-wave pulses (5.0 msec. in duration, three times threshold voltage) delivered through the hook electrode and a second electrode positioned near the top of the muscle evoked 12 contractions/minute, which were recorded on a Grass polygraph. After the muscles had equilibrated for 60 minutes, the recorder gain was adjusted so that the pen deflected 10 mm. The test compound was introduced in a solution of normal saline in an amount to bring the final concentration of the compound to $10^{-5}$ or $10^{-4}$ molar. Increases in contractility were tabulated as millimeters of pen deflection in excess of the baseline value. In each experiment the maximum contractility was measured. Test results are summarized in Table I and are expressed as percent of control (control=100 percent). Values are the average of results from 2 to 8 muscles.

TABLE I

| | Effects of Compounds on Contractility in Cat Papillary Muscles | |
|---|---|---|
| | Contractility of Papillary Muscle* | |
| | Compound Concentration | |
| Compound | $10^{-5}$ M | $10^{-4}$ M |
| Example 1 | 202 | 208 |
| Compound A | 147 | 152 |
| Compound B | 178 | 169 |

*Data are peak responses at the indicated concentration of compound and are expressed as a percent of control (control = 100 percent).

Experiments in Anesthetized Dogs

Mongrel dogs of either sex ranging in weight for 7 to 14 kg were used. Anesthesia was induced with sodium pentobarbital (30 mg/kg, i.v.) and maintained with supplemental doses as required. A positive-pressure pump was used to ventilate the dogs through an endotracheal tube (18 strokes/minute, 20 ml/kg $stroke^{-1}$), and a heating pad kept the body temperature at 37°–38° C.

Femoral arterial blood pressure was measured through a polyethylene catheter filled with heparin solution (16 units/ml) and connected to a Statham pressure transducer. A strain-gauge arch sutured to the right ventricle of the heart measured cardiac contractility. Tension on the gauge was adjusted to 50 g and the gain of the recorder (Beckman dynograph) was set so that 50 g caused a 10-mm pen deflection. Cardiac contractile tension was measured as millimeters of pen deflection or grams of tension. The test compounds were administered as an i.v. bolus (2–5 ml) in a normal saline vehicle following a 30–45 minute equilibrium period. In a control experiment, rapid intravenous injection of 50 ml of 5 percent dextran and mechanical compression of the aorta showed that the contractility measurements were independent of changes in preload and afterload. Heart rate was derived by means of a cardiotach which was triggered by the arterial pressure pulse signal and displayed on the polygraph. The maximum effects on contractility at various dose levels were determined and plotted and the dose required to produce a 50% increase in contractility ($ED_{50}$) was determined by interpolation. The $ED_{50}$'s for each compound tested are summarized in Table II.

TABLE II

| Effects of Compounds on Ventricular Contractility in the Anesthetized dog | |
|---|---|
| Compound | $ED_{50}$ (mcg/kg)* |
| Example 1 | 5 |
| Example 2 | 10 |
| Example 3 | 5 |
| Example 4 | 8.5 |
| Example 5 | 20 |
| Example 6 | 21 |
| Example 7 | 2.5 |
| Example 8 | 6.3 |
| Compound A | 10 |
| Compound B | 48 |

*i.v. dose required to produce a peak increase in contractility of 50%.

Experiments in Conscious Dogs

Mongrel dogs of either sex weighing 15–36 kg were chronically instrumented to monitor peak systolic pressure, heart rate, left ventricular pressure and its first derivative, LVdP/dt at 60 mm of mercury. Under halothane-nitrous oxide anesthesia, a precalibrated Konigsberg P22 Pressure Transducer was implanted into the left ventricle through a stab wound at the apex. Following recovery from surgery, a minimum of two weeks was allowed to train the dogs to lie quietly for four-hour periods. This conditioning was necessary to obtain stable, reproducible results from day to day. Dogs were fasted eighteen hours before an experiment. Gross behavioral observations of animals were made throughout each study. Compounds or placebo (lactose) were administered in gelatin capsules. The maximum effects on contractility at various dose levels were determined and plotted and the dose required to produce a 50-percent increase in contractility ($ED_{50}$) was determined by interpolation. The $ED_{50}$'s for each compound tested are summarized in Table III.

TABLE III

Effects of Compounds on Ventricular Contractility in the Conscious Dog

| Compound | $ED_{50}$ (mcg/kg)* |
|---|---|
| Example 1 | 25 |
| Example 2 | >400 |
| Example 7 | 50 |
| Example 8 | 25 |
| Compound A | 500 |
| Compound B | >500 |

*oral dose required to produce a peak increase in contractility of 50%.

The compounds of this invention may be administered by various routes including the oral, rectal, transdermal, subcutaneous, intravenous, intramuscular, or intranasal routes. It is a special feature of these compounds that they are effective positive inotropic agents, vasodilators, or bronchodilators following oral administration. The compounds are usually employed in the form of pharmaceutical compositions. Such compositions are prepared in a manner well known in the pharmaceutical art and comprise at least one active compound. Accordingly, the invention includes a pharmaceutical composition comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The compositions ususally contain active ingredient from about 1% to about 95% by weight and are preferably formulated in a unit dosage form, each dosage containing from about 0.5 to about 500 mg, more usually 1 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The active compounds are effective over a wide dosage range and typical dosages per day will normally fall within the range of about 0.020 to about 300 mg/kg of body weight. In the treatment of adult humans, a range of from about 0.020 to about 50 mg/kg, in single or divided doses, is preferred. However, it will be understood that the amount of the compound actually administered will be determined by a physician in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingedients any of the pharmaceutical compounds of the invention. The examples are illustrative only and are not intended to limit the scope of the invention in any way.

EXAMPLE 9

Hard gelatin capsules are prepared using the following ingredients:

| | Quantity (mg/capsule) |
|---|---|
| 1,3-dihydro-3,3-dimethyl-5-(1,4,5,6-tetrahydro-6-oxo-3-pyridazinyl)-2H—indol-2-one | 250 |
| Starch dried | 200 |
| Magnesium stearate | 10 |

The above ingredients are mixed and filled into hard gelatin capsules in 460 mg quantities.

EXAMPLE 10

A tablet formula is prepared using the ingredients below:

| | Quantity (mg/tablet) |
|---|---|
| 1,3-dihydro-3,3-dimethyl-5-(1,4,5,6-tetrahydro-4-methyl-6-oxo-3-pyridazinyl)-2H—indol-2-one | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 11

An aerosol solution is prepared containing the following components:

| | Weight % |
|---|---|
| 3,3-dimethyl-5-(1,4,5,6-tetra- | 0.25 |

| | Weight % |
|---|---|
| hydro-6-oxo-3-pyridazinyl)-indoline | |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remaining amount of propellant. The valve units are then fitted to the container.

EXAMPLE 12

Tablets each containing 60 mg of active ingredient are made up as follows:

| | |
|---|---|
| 1,3-dihydro-1-acetyl-3,3-dimethyl-5-(1,4,5,6-tetrahydro-4-methyl-6-oxo-3-pyridazinyl)-2H—indol-2-one | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg. |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 13

Capsules each containing 80 mg of medicament are made as follows:

| | |
|---|---|
| 1,3,3-trimethyl-5-(1,4,5,6-tetrahydro-4,4-diethyl-6-oxo-3-pyridazinyl)indoline | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 14

Suppositories each containing 225 mg of active ingredient are made as follows:

| | |
|---|---|
| 1,3-dihydro-1-(3,4-dichloro-benzoyl)-3,3-dimethyl-5-(1,6-dihydro-4-isopropyl-6-oxo-3-pyridazinyl )-2H—indol-2-one | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 15

Suspensions each containing 50 mg of medicament per 5 ml dose are made as follows:

| | |
|---|---|
| 1,3-dihydro-3,3-dimethyl-5-(1,4,5,6-tetrahydro-1-hydroxy-methyl-4-methyl-6-oxo-3-pyridazinyl)-2H—indol-2-one | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

I claim:

1. A compound of the formula

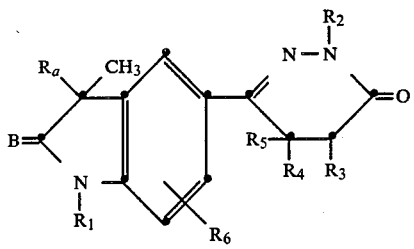

wherein:
$R_a$ is hydrogen or methyl;
$B=C<$ is $O=C<$ or $H_2C<$;
$R_1$ is hydrogen, $C_1$–$C_4$ alkyl, $C_2$–$C_4$ alkanoyl, methyl- or ethyl-sulfonyl, or benzoyl optionally substituted on the phenyl ring with one to three substituents selected from halo, $C_1$–$C_4$ alkyl, methoxy or ethoxy;
$R_2$ is hydrogen, $C_1$–$C_{22}$ alkyl, hydroxy-substituted $C_1$–$C_3$ alkyl, carbamoyl-substituted $C_1$–$C_{11}$ alkyl, naphthyloxy-methyl or -ethyl, an oxo-substituted $C_1$–$C_{11}$ alkyl group, or $R_6R_7N$—$(CH_2)_n$— where each of $R_6$ and $R_7$ is independently hydrogen or $C_1$–$C_4$ alkyl, or when taken together with the nitrogen atom to which they are attached form a pyrrolidino, piperidino, morpholino, piperazino, or N-methylpiperazino ring, and n is 2 or 3;
$R_3$ is hydrogen or methyl;
$R_4$ is hydrogen, $C_1$–$C_4$ alkyl, hydroxymethyl, or $C_2$–$C_4$ alkanoyloxymethyl;
$R_5$ is hydrogen or $C_1$–$C_4$ alkyl;

or $R_3$ and one of $R_4$ and $R_5$ taken together form a bond;

$R_6$ is hydrogen or methyl; or a pharmaceutically acceptable salt thereof.

2. A compound according to claim 1 wherein $B=C<$ is $O=C<$.

3. A compound according to claim 2 wherein each of $R_1$, $R_2$, and $R_3$ is hydrogen.

4. A compound according to claim 3 wherein $R_5$ is hydrogen.

5. The compound of claim 4 which is 1,3-dihydro-3,3-dimethyl-5-(1,4,5,6-tetrahydro-6-oxo-3-pyridazinyl)-2H-indol-2-one or a pharmaceutically acceptable salt thereof.

6. A compound according to claim 3 wherein $R_5$ is methyl.

7. The compound of claim 6 which is 1,3-dihydro-3,3-dimethyl-5-(1,4,5,6-tetrahydro-4-methyl-6-oxo-3-pyridazinyl)-2H-indol-2-one or a pharmaceutically acceptable salt thereof.

8. A method of producing a positive inotropic effect in a mammal, which comprises administering to said mammal an effective amount of a compound of claim 1.

9. The method according to claim 8 employing a compound wherein $B=C<$ is $O=C<$.

10. The method according to claim 9 employing a compound wherein each of $R_1$, $R_2$, and $R_3$ is hydrogen.

11. The method according to claim 10 employing a compound wherein $R_5$ is hydrogen or methyl.

12. The method of claim 11 employing 1,3-dihydro-3,3-dimethyl-5-(1,4,5,6-tetrahydro-6-oxo-3-pyridazinyl)-2H-indol-2-one or a pharmaceutically acceptable salt thereof.

13. The method of claim 11 employing 1,3-dihydro-3,3-dimethyl-5-(1,4,5,6-tetrahydro-4-methyl-6-oxo-3-pyridazinyl)-2H-indol-2-one or a pharmaceutically acceptable salt thereof.

14. A pharmaceutical formulation which comprises a compound of claim 1 in association with a pharmaceutical carrier.

15. A formulation according to claim 14 employing a compound wherein $B=C<$ is $O=C<$.

16. A formulation according to claim 15 employing a compound wherein each of $R_1$, $R_2$, and $R_3$ is hydrogen.

17. A formulation according to claim 16 employing a compound wherein $R_5$ is hydrogen.

18. A formulation according to claim 17 employing 1,3-dihydro-3,3-dimethyl-5-(1,4,5,6-tetrahydro-6-oxo-3-pyridazinyl)-2H-indol-2-one or a pharmaceutically acceptable salt thereof.

19. A formulation according to claim 16 employing a compound wherein $R_5$ is methyl.

20. A formulation according to claim 19 employing 1,3-dihydro-3,3-dimethyl-5-(1,4,5,6-tetrahydro-4-methyl-6-oxo-3-pyridazinyl)-2H-indol-2-one or a pharmaceutically acceptable salt thereof.

* * * * *